US011524068B2

(12) United States Patent
Tucker et al.

(10) Patent No.: US 11,524,068 B2
(45) Date of Patent: *Dec. 13, 2022

(54) METHODS OF VACCINE ADMINISTRATION

(71) Applicant: Zoetis Services LLC, Parsippany, NJ (US)

(72) Inventors: Cassius McAllister Tucker, Kalamazoo, MI (US); John David Haworth, Englewood, CO (US)

(73) Assignee: Zoetis Services LLC, Parsippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/910,284

(22) Filed: Jun. 24, 2020

(65) Prior Publication Data
US 2020/0316192 A1 Oct. 8, 2020

Related U.S. Application Data

(63) Continuation of application No. 14/282,702, filed on May 20, 2014, which is a continuation of application No. 12/521,148, filed as application No. PCT/IB2007/003666 on Nov. 23, 2007, now abandoned.

(60) Provisional application No. 60/877,322, filed on Dec. 27, 2006.

(51) Int. Cl.
*A61K 39/175* (2006.01)
*A61K 39/295* (2006.01)
*A61K 39/00* (2006.01)
*A61K 39/38* (2006.01)
*A61K 39/235* (2006.01)
*A61K 39/02* (2006.01)
*A61K 39/12* (2006.01)
*A61K 39/155* (2006.01)
*A61K 39/23* (2006.01)
*C07K 14/005* (2006.01)
*C12N 7/00* (2006.01)

(52) U.S. Cl.
CPC ........ *A61K 39/235* (2013.01); *A61K 39/0225* (2013.01); *A61K 39/099* (2013.01); *A61K 39/12* (2013.01); *A61K 39/155* (2013.01); *A61K 39/175* (2013.01); *A61K 39/23* (2013.01); *C07K 14/005* (2013.01); *C12N 7/00* (2013.01); *A61K 39/00* (2013.01); *A61K 2039/525* (2013.01); *A61K 2039/5254* (2013.01); *A61K 2039/542* (2013.01); *A61K 2039/545* (2013.01); *A61K 2039/552* (2013.01); *A61K 2039/70* (2013.01); *C12N 2710/10034* (2013.01); *C12N 2710/10071* (2013.01); *C12N 2710/10334* (2013.01); *C12N 2750/14034* (2013.01); *C12N 2750/14071* (2013.01); *C12N 2750/14334* (2013.01); *C12N 2760/18034* (2013.01); *C12N 2760/18071* (2013.01); *C12N 2760/18434* (2013.01); *C12N 2760/18471* (2013.01); *C12N 2770/20022* (2013.01)

(58) Field of Classification Search
CPC ... A61K 39/175; A61K 39/235; A61K 39/099
See application file for complete search history.

(56) References Cited

U.S. PATENT DOCUMENTS

| 4,752,474 A | 6/1988 | Schneider | |
| 5,000,951 A * | 3/1991 | Bass | A61K 39/175 424/201.1 |
| 5,013,663 A * | 5/1991 | Acree | A61K 39/215 424/221.1 |
| 5,178,862 A * | 1/1993 | Olsen | C07K 14/005 424/213.1 |
| 5,747,063 A | 5/1998 | Languet et al. | |
| 2004/0185062 A1* | 9/2004 | Dominowski | A61K 39/23 424/190.1 |
| 2005/0089533 A1* | 4/2005 | Frantz | A61K 39/39 424/234.1 |
| 2015/0182619 A1* | 7/2015 | Tucker | A61P 37/04 424/201.1 |

FOREIGN PATENT DOCUMENTS

| WO | WO 98/18453 A1 | 5/1998 |
| WO | WO 02/02139 A2 | 1/2002 |
| WO | WO 2004/067031 A1 | 8/2004 |
| WO | WO 2006/038115 A1 | 4/2006 |

OTHER PUBLICATIONS

A document submitted in the opposition proceedings against Australian Patent Application No. 2017203965—Written Submissions of Zoetis Services LLC Hearing Date: Sep. 1, 2021.
A document submitted in the opposition proceedings against Australian Patent Application No. 2015255165 dated Jun. 15, 2016.
A document submitted in the opposition proceedings against Australian Patent Application No. 2019204604—Examination report No. 1 for standard patent application dated Jul. 27, 2020.
A document submitted in the opposition proceedings against Australian Patent Application No. 2013201732—Patent Examination Report No. 1 dated Feb. 13, 2014.

(Continued)

Primary Examiner — Brian Gangle
Assistant Examiner — Lakia J Jackson-Tongue
(74) Attorney, Agent, or Firm — Vyacheslav Vasilyev

(57) ABSTRACT

This invention relates to a method of treating a dog for canine diseases comprising administering to the dog therapeutically effective amounts of a vaccine, wherein the vaccine comprises viral antigens, a bacterin, or both, and wherein the vaccine is administered subcutaneously or orally according to the schedules provided herein.

14 Claims, 3 Drawing Sheets

(56) References Cited

OTHER PUBLICATIONS

A document submitted in the opposition proceedings against New Zealand Patent 577855—Applicant for Revocation's Outline of Submissions, Jun. 17, 2021.
A document submitted in the opposition proceedings against New Zealand Patent Application 577855—Amended Statement of Case—clean—Aug. 7, 2014.
A document submitted in the opposition proceedings against New Zealand Patent No. 577855—Supplementary Counterstatement, dated Feb. 13, 2015.
A document submitted in the opposition proceedings against New Zealand Patent Application 577855—Statement of Case, Jan. 2, 2014.
A document submitted in the opposition proceedings against New Zealand Patent Application 577855—Amended Statement of Case, Jul. 10, 2014.
A document submitted in the opposition proceedings against New Zealand Patent 577855—Amended Application for the Revocation of a Patent (Section 42)—marked up—Aug. 7, 2014.
A document submitted in the opposition proceedings against New Zealand Patent 577855—Statutory Declaration of Richard Bevan, dated Apr. 24, 2015.
A document submitted in the opposition proceedings against New Zealand Patent 577855—Statutory Declaration of Karin Marie Innes, dated Jul. 10, 2014.
Statutory Declaration of Marilyn Domney dated Jul. 9, 2014.
A document submitted in the opposition proceedings against New Zealand Patent 577855—Statutory Declaration of Steven A. Holloway dated Feb. 19, 2015.
A document submitted in the opposition proceedings against New Zealand Patent 577855—Exhibits D32 and D33 referred to in the Amended Statement of Case.
A document submitted in the opposition proceedings against New Zealand Patent 577855—Patents Form 45—Application under Section 42 for the Revocation of a Patent dated Nov. 4, 2013; and (ii) Patent Form 76—Extension of time application to file a Statement of Case dated Nov. 4, 2013.
A document submitted in the opposition proceedings against New Zealand Patent 577855—Amended Statement of Case—marked up—dated Jul. 10, 2014.
A document submitted in the opposition proceedings against New Zealand Patent 577855—Counterstatement, dated Mar. 5, 2014.
A document submitted in the opposition proceedings against New Zealand Patent 577855—Amended Statement of Case—marked up—dated Aug. 7, 2014.
A document submitted in the opposition proceedings against New Zealand Patent 577855—Amended Application for the Revocation of a Patent (Section 42), dated Aug. 7, 2014.
A document submitted in the opposition proceedings against New Zealand Patent 577855—Statutory Declaration of Jenny Petering dated Apr. 28, 2015.
Statutory Declaration of Marilyn Domney dated Apr. 28, 2015.
A document submitted in the opposition proceedings against New Zealand Patent 577855—Statutory Declaration of Richard Bevan dated Jul. 12, 2014.
Product Registration Vanguard Plus 5 vaccine.
A document submitted in the opposition proceedings against New Zealand Patent 577855—Synopsis of Submissions of Counsel for the Patentee dated Jun. 24, 2021.
A document submitted in the matter of Australian Patent Application 2017203965—Keith Ameiss Declaration dated Sep. 16, 2020.
A document submitted in the matter of Australian Patent Acceptance 2007343130—Annexure A referred to in Richard Bevan's Declaration made on Jun. 16, 2015.
A document submitted in the matter of Australian Patent Acceptance 2007343130—Richard Bevan Declaration dated May 15, 2014.
A document submitted in the matter of Australian Patent Acceptance 2007343130—Richard Bevan Declaration dated May 15, 2014 (with exhibits).
A document submitted in the matter of Australian Patent Application 2017203965—BIVI comments—Outline of Submissions—dated Aug. 18, 2021.
A document submitted in the matter of Australian Patent Application 2017203965—BIVI—Statement of Grounds and Particulars dated Jan. 17, 2020.
A document submitted in the matter of Australian Patent Application 2017203965—Terry L. Bowersock Declaration dated Sep. 11, 2020.
A document submitted in the matter of Australian Patent Acceptance 2007343130—Michele Brettmann Declaration dated May 8, 2015.
A document submitted in the matter of Australian Patent Acceptance 2007343130, Decision dated May 11, 2018.
A document submitted in the matter of Australian Patent Acceptance 2007343130—Decision dated May 5, 2017.
A document submitted in the matter of Australian Patent Acceptance 2007343130—Decision dated Mar. 7, 2016.
A document submitted in the matter of Australian Patent Acceptance 2007343130—Patent Oppositions—Decision Issued—Jul. 7, 2015.
A document submitted in the matter of Australian Patent Acceptance 2007343130—Patent Oppositions—Decision dated May 5, 2017.
A document submitted in the matter of Australian Patent Acceptance 2007343130—Exhibits KA-1-13 KA-3 referred to in the Statutory Declaration of Keith Ameiss dated this Sep. 16, 2020.
A document submitted in the matter of Australian Patent Acceptance 2007343130—Exhibit TLB-1 referred to in the Statutory Declaration of Terry L. Bowersock dated this Sep. 11, 2020.
A document submitted in the matter of Australian Patent Acceptance 2007343130—Exhibit SW-1 referred to in the Statutory Declaration of Sharon Wappel dated this Sep. 16, 2020.
A document submitted in the matter of Australian Patent Acceptance 2007343130—Steven A Holloway, Declaration, dated Dec. 19, 2013.
A document submitted in the matter of Australian Patent Application No. 2007343130—Further Evidence Written Submissions of Zoetis P LLC dated Jun. 23, 2015.
A document submitted in the matter of Australian Patent Application No. 2007343130—Statement of Grounds and Particulars dated Jun. 20, 2013.
A document submitted in the matter of Australian Patent Application No. 2007343130—Statement of Grounds and Particulars dated May 20, 2014.
A document submitted in the matter of Australian Patent Application No. 2007343130—Amended Statement of Grounds and Particulars dated Nov. 13, 2013.
A document submitted in the matter of Australian Patent Application 2017203965—Steven A. Holloway Declaration Exhibits.
A document submitted in the matter of Australian Patent Application 2017203965—Steven A. Holloway, Declaration dated Nov. 17, 2020.
A document submitted in the matter of Australian Patent Acceptance 2007343130—Annexure B referred to in Karin Innes Declaration made on Jun. 16, 2015.
A document submitted in the matter of Australian Patent Acceptance 2007343130—Annexure A referred to in Karin Innes Declaration made on Jun. 16, 2015.
A document submitted in the matter of Australian Patent Acceptance 2007343130—Karin Innes, Declaration date Jun. 16, 2015.
Label 1—Final Container.
Label 2—date submitted Nov. 10, 2005.
Label 3—date submitted Nov. 10, 2005.
Label 4—date submitted Jul. 2, 2004.
Label 5—date submitted Mar. 28, 2006.
Label 6—date submitted Mar. 28, 2006.
Label 7—date submitted Dec. 19, 2005.
Label 8—date submitted Jul. 2, 2004.
A document submitted in the matter of Australian Patent Acceptance 2007343130—Sally Kim Mannion Declaration dated Dec. 7, 2015.
A document submitted in The matter of Australian Patent Acceptance 2007343130—Merial Submission 1.
A document submitted in The matter of Australian Patent Acceptance 2007343130—Merial Submission 2.

(56) References Cited

OTHER PUBLICATIONS

A document submitted in The matter of Australian Patent Acceptance 2007343130—Robert M. Nordgren Declaration dated Nov. 6, 2015.
A document submitted in The matter of Australian Patent Acceptance 2007343130—Robert M. Nordgren Declaration dated Nov. 6, 2015 with Exhibit 1.
A document submitted in the matter of Australian Patent Application 2017203965—Exhibits RMN-14-RMN-16 referred to in the Statutory Declaration of Robert M Nordgren dated this Apr. 19, 2021.
A document submitted in the matter of Australian Patent Application 2017203965—Robert M. Nordgren Declaration dated Apr. 16, 2020.
A document submitted in The matter of Australian Patent Acceptance 2007343130—Opponent Submission of Jan. 9, 2018.
A document submitted in The matter of Australian Patent Acceptance 2007343130—Report of Jul. 7, 2015—Patent Oppositions—Decision Issued.
A document submitted in The matter of Australian Patent Acceptance 2007343130—Examiner's first report on patent application No. 2007343130 dated May 29, 2012.
A document submitted in The matter of Australian Patent Acceptance 2007343130—Second Steven A. Holloway Declaration dated Feb. 20, 2014.
A document submitted in the matter of Australian Patent Application 2017203965—Exhibits TS-1-TS-3 referred to in the Declaration of Tony Shaw dated Sep. 17, 2020.
A document submitted in the matter of Australian Patent Application 2017203965—Tony Shaw Declaration dated Sep. 17, 2020.
A document submitted in the matter of Australian Patent Acceptance 2007343130—Submissions of the Opponent Opposition to Application to file further Evidence Made May 11, 2015.
A document submitted in The matter of Australian Patent Acceptance 2007343130—Submissions of the Opponent Further Evidence and Want of Manner of Manufacture Feb. 4, 2016.
A document submitted in The matter of Australian Patent Acceptance 2007343130—Written Submissions of Zoetis P LLC Feb. 9, 2015.
A document submitted in The matter of Australian Patent Acceptance 2007343130—Reply Submissions of the Opponent Opposition to Application to File Further Evidence Made May 11,2015—dated Jun. 23, 2015.
A document submitted in The matter of Australian Patent Acceptance 2007343130—Submissions of the Opponent Feb. 13, 2017.
A document submitted in The matter of Australian Patent Acceptance 2007343130—Written Submissions of Zoetis P LLC dated Jun. 16, 2015.
A document submitted in The matter of Australian Patent Acceptance 2007343130—Written Submissions of Zoetis P LLC Hearing dated May 6, 2015.
A document submitted in The matter of Australian Patent Acceptance 2007343130—Third Steven A. Holloway Declaration dated Aug. 11, 2014.
A document submitted in the matter of Australian Patent Application 2017203965—Sharon Wappel Declaration dated Sep. 16, 2020.
A document submitted in the matter of Australian Patent Acceptance 2007343130—Written Submissions of Zoetis Services LLC dated Jan. 25, 2018.
A document submitted in the matter of Australian Patent Acceptance 2007343130—Written Submissions of Zoetis Services LLC Hearing Date Feb. 24, 2017, dated Feb. 20, 2017.
M. J. Coyne, et al., "Duration of immunity in dogs after vaccination or naturally acquired infection," The Veterinary Record, Oct. 27, 2001, pp. 509-515.
Roland Estrada, et al., "Acceptability of local made baits for oral vaccination of dogs against rabies in the Philippines," BMC Infectious Diseases 2001, 1:19, pp. 1-5.
Alessio Fasano, "Innovative strategies for the oral delivery of drugs and peptides," TIBTECH Apr. 1998 (vol. 16), pp. 152-157.
H. Kuntsi-Vaattovaara, et al., "Resolution of persistent oral papillomatosis in a dog after treatment with a recombinant canine oral papillomavirus vaccine," Veterinary and Comparative Oncology, 2003, 1, 1, pp. 57-63.
Douglas E. Mouzin, et al., "Duration of serologic response to five viral antigens in dogs," JAVMA, vol. 224, No. 1, Jan. 1, 2004, pp. 55-60.
O. Zwisler, et al., "Oral Immunization of Dogs against Tetanus, Diphtheria and Pertussis," 15$^{th}$ IABS Congress: Vaccinations in the Developing Countries, La Guadeloupe 1978. Develop. Biol. Standard., vol. 41, pp. 39-43 (S. Karger, Basel 1978).
Patent Board Decision and Oral Hearing Transcript dated Oct. 20, 2021 for Appeal 2021-000783, U.S. Appl. No. 14/282,702.
A Decision submitted in the matter of a New Zealand Patent No. 577855, in the name of Zoetis P LLC (patentee) and of an application for revocation under section 42 by Merial Limited (applicant) dated Aug. 31, 2022.

* cited by examiner

Figure 1. Serological Response (SN) to CDV (mean titers)

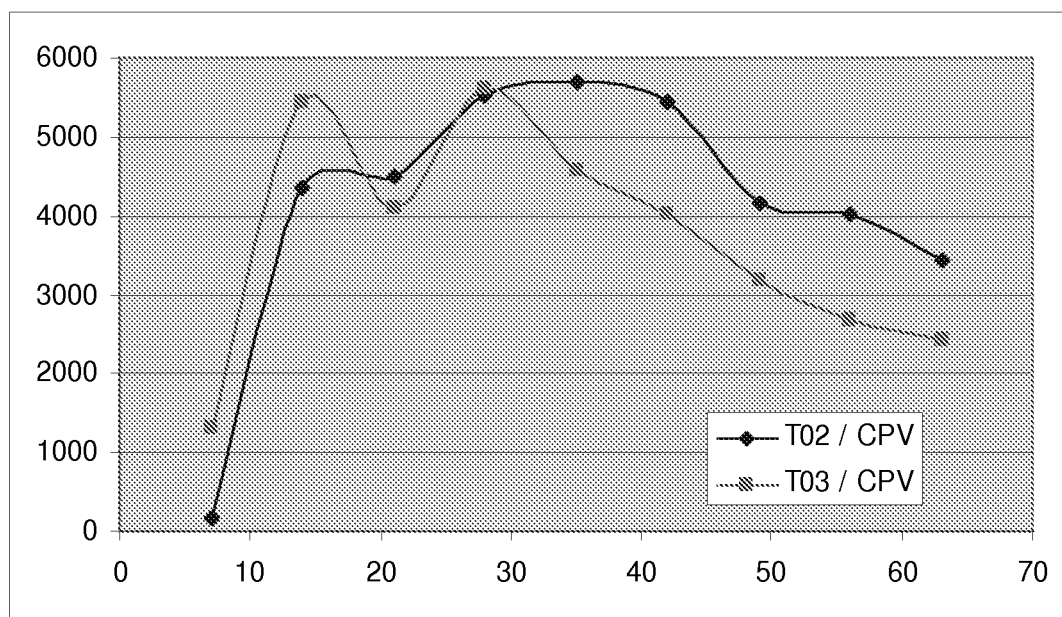
Figure 2. Serological Response (SN) to CPV (mean titers)

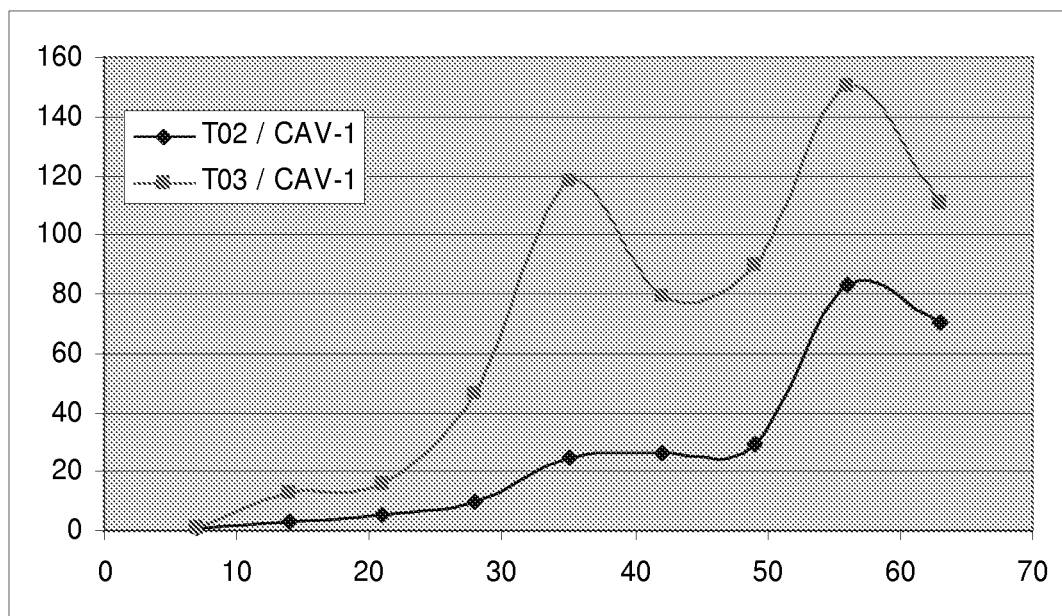
Figure 3. Serological Response (SN) to CAV-1 (mean titers)

METHODS OF VACCINE ADMINISTRATION

CROSS-REFERENCE TO RELATED APPLICATIONS

This application is a continuation of U.S. application Ser. No. 14/282,702 filed on May 20, 2014, which is a continuation of U.S. application Ser. No. 12/521,148, filed Jun. 25, 2009, which is a National Stage entry of PCT/IB07/03666 filed on November 2007, which claims priority to U.S. Provisional Application Ser. No. 60/877,322 filed Dec. 27, 2006.

FIELD OF INVENTION

This invention relates to a method of treating a dog for canine diseases comprising administering to the dog therapeutically effective amounts of vaccine, wherein the vaccine comprises viral antigens, a bacterin, or both, and wherein the vaccine is administered subcutaneously or orally according to the schedules provided herein.

BACKGROUND OF THE INVENTION

Vaccines against major canine infectious disease have been available for three to four decades, and they have greatly reduced the incidence of these infectious diseases in dogs (Appel, M J. 1999. Adv Vet Med. 41:309-324). Pfizer Animal Health sells several vaccines for prevention of diseases associated with various viral and bacterial diseases in dogs. The VANGUARD® line of vaccines, including core canine vaccines, is used for the vaccination of healthy dogs 6 weeks of age or older as an aid in preventing canine distemper (CD) caused by canine distemper (CD) virus, infectious canine hepatitis (ICH) caused by canine adenovirus type 1 (CAV-1), respiratory disease caused by canine adenovirus type 2 (CAV-2), canine parainfluenza (CPI) caused by canine parainfluenza (CPI) virus, and canine parvoviral enteritis caused by canine parvovirus (CPV) (Mouzin D E, et al., 2004, JAVMA, 224: 55-60).

CD is a high morbidity, high mortality viral disease occurring in unvaccinated dog populations worldwide. Approximately 50% of non-vaccinated, non-immune dogs infected with CDV develop clinical signs and approximately 90% of those dogs die (Swango L J. 1983. Norden News 58:4-10). ICH, caused by CAV-1, is a universal, sometimes fatal, viral disease of dogs characterized by hepatic and generalized endothelial lesions. The respiratory disease caused by CAV-2, in severe cases, may include pneumonia and bronchopneumonia. CAV-2 vaccine has been shown to cross-protect against ICH caused by CAV-1 (Bass E P, et al., 1980, JAVMA, 177:234-242). The upper respiratory disease caused by CPI virus may be mild or subclinical, with signs becoming more severe if concurrent infection with other respiratory pathogens exists. The enteric disease caused by CPV is characterized by sudden onset of vomiting and diarrhea, often hemorrhagic, and may be accompanied by leukopenia (Appel M J, et al., 1979, Vet Rec, 105:156-159).

Major animal health companies market core canine vaccines in their companion animal vaccine franchise. However, all of these vaccines are delivered by the parenteral route, especially subcutaneous injections. A canine vaccine that could be delivered easily would provide increased convenience of vaccine delivery to the pet, the veterinarian, and the pet owner, and allow for personnel untrained in parenteral administration techniques to deliver canine core vaccines to animals.

SUMMARY OF THE INVENTION

Provided herein is a method of treating a dog for canine diseases comprising administering to the dog therapeutically effective amounts of vaccine, wherein the vaccine comprises viral antigens, a bacterin, or both, and wherein the vaccine is administered subcutaneously or orally in a first dose, orally in a second dose, orally in an optional third dose, and orally in one or more annual doses. The viral antigens comprise one or more of 1) canine distemper (CD) virus, 2) canine adenovirus type 2 (CAV-2), 3) canine parainfluenza (CPI) virus, 4) canine parvovirus (CPV), 5) and canine coronavirus (CCV), and wherein the bacterin comprises one or more of *Leptospira canicola, L. grippotyphosa, L. icterohaemorrhagiae, L. Pomona, L. bratislava*, and *Bordetella bronchiseptica*; and any combination of viral antigens and bacterin thereof.

Also provided herein is a method of treating a dog for canine diseases comprising administering to the dog therapeutically effective amounts of vaccine, wherein the vaccine comprises viral antigens, a bacterin, or both, and wherein the vaccine is administered subcutaneously in a first and in a second dose, and orally in a third dose, and orally in one or more annual doses. The viral antigens comprise one or more of 1) CD virus, 2) CAV-2, 3) CPI virus, 4) CPV, 5) and CCV, and the bacterin comprises one or more of *Leptospira canicola, L. grippotyphosa, L. icterohaemorrhagiae, L. Pomona, L. bratislava*, and *Bordetella bronchiseptica*; and any combination of viral antigens and bacterin thereof.

In one embodiment, the vaccine comprises one or more live viruses, one or more modified-live viruses, one or more inactivated viruses, or combinations thereof.

In one embodiment, the viral antigens are CD virus, CAV-2, CPI virus, and CPV. In another embodiment, these four viral antigens are combined with a bacterin composed of *Leptospira canicola, L. grippotyphosa, L. icterohaemorrhagiae*, and *L. pomona*. In yet another embodiment, these four viral antigens are combined with a bacterin composed of *Bordetella bronchiseptica*. In still another embodiment, these four viral antigens are combined with the CCV antigen and a bacterin composed of *Leptospira canicola, L. grippotyphosa, L. icterohaemorrhagiae*, and *L. pomona*.

The treated canine diseases comprise one or more of the following: 1) CD caused by CD virus; 2) infectious canine hepatitis caused by CAV-1; 3) respiratory disease caused by CAV-2 or respiratory CCV; 4) CPI caused by CPI virus; 5) enteritis caused by CCV or CPV; 6) leptospirosis caused by *Leptospira canicola, L. grippotyphosa, L. icterohaemorrhagiae, L. pomona*, or *L. Bratislava*; and 7) infectious tracheobronchitis ("kennel cough") caused by *Bordetella bronchiseptica*.

In one embodiment, the treated diseases comprise 1) CD caused by CD virus; 2) infectious canine hepatitis caused by CAV-1; 3) respiratory disease caused by CAV-2; 4) CPI caused by CPI virus; 5) and canine parvoviral enteritis caused by CPV.

In one embodiment, the second dose is administered from about 7 to about 35 days, inclusive, after the first dose. In a more specific embodiment, the second dose is administered about 3 weeks after the first dose. In another embodiment, the third dose is administered from about 7 to about 35 days, inclusive, after the second dose. In a more specific embodiment, the third dose is administered about 3 weeks after the second dose. In still another embodiment, the annual dose is administered about one year after the first dose. In yet another embodiment, annual doses administered after said annual dose are administered repeatedly about one year after the immediately prior annual dose.

BRIEF DESCRIPTION OF THE DRAWINGS

FIG. 1. Serological Response (SN) to CDV (mean titers). Animals in treatment groups T02 and T03 were given experimental vaccines first subcutaneously (on day 0), then the same vaccine orally three weeks (day 21) and six weeks (day 42) later. The animals in group T02 received a relatively low dose, and the animals in group T03 received a relatively high dose. Blood samples were taken weekly to measure concentrations (e.g., titers) of CDV.

FIG. 2. Serological Response (SN) to CPV (mean titers). Animals were treated as described for FIG. 1. Blood samples were taken weekly to measure concentrations (e.g., titers) of CPV.

FIG. 3. Serological Response (SN) to CAV-1 (mean titers). Animals were treated as described for FIG. 1. Blood samples were taken weekly to measure concentrations (e.g., titers) of CAV-1.

DETAILED DESCRIPTION OF THE INVENTION

Definitions and Abbreviations

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means a pharmaceutically acceptable substance or composition that increases the immune response to an antigen.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to killed, attenuated or inactivated bacteria or viruses. The term antigen also refers to antibodies, such as anti-idiotype antibodies or fragments thereof, and to synthetic peptide mimotopes that can mimic an antigen or antigenic determinant (epitope).

"Excipient" refers to any component of a vaccine that is not an antigen.

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

"Immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunologically protective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune response or antigenic. Thus an immunogenic composition would be any composition that induces an immune response.

"Intranasal" means within the nose. Thus, intranasal administration refers to the introduction of a substance, such as a vaccine, into a subject's body through or by way of the nose, as would occur, for example, by placing one or more droplets in the nose. It involves transport of the substance primarily through the nasal and nasopharyngeal mucosa.

"N days," "N" interval or period of time, or "M days" following an event refers, respectively, to any time on the N th or M th day after the event. For example, vaccinating a subject with a second vaccine 21 days following administration of a first vaccine means that the second vaccine is administered at any time on the $21^{st}$ day after the first vaccine. This description is often applied to the interval between a first and second vaccination, or between a second and third vaccination.

"Oral" or "peroral" administration refers to the introduction of a substance, such as a vaccine, into a subject's body through or by way of the mouth and involves swallowing or transport through the oral mucosa (e.g., sublingual or buccal absorption) or both.

"Oronasal" administration refers to the introduction of a substance, such as a vaccine, into a subject's body through or by way of the nose and the mouth, as would occur, for example, by placing one or more droplets in the nose. Oronasal administration involves transport processes associated with oral and intranasal administration.

"Parenteral administration" refers to the introduction of a substance, such as a vaccine, into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration. For the purposes of this disclosure, parenteral administration excludes administration routes that primarily involve transport of the substance through mucosal tissue in the mouth, nose, trachea, and lungs.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Subject" refers to a canine.

"$TCID_{50}$" refers to "tissue culture infective dose" and is defined as that dilution of a virus required to infect 50% of a given batch of inoculated cell cultures. Various methods known to one skilled in the art may be used to calculate $TCID_{50}$, including the Spearman-Karber method which is utilized throughout this specification. For a description of the Spearman-Karber method, see B. W. Mahy & H. O. Kangro, *Virology Methods Manual* 25-46 (1996).

"Therapeutically effective amount," in the context of this disclosure, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and can be determined by a veterinary physician.

"Treating" refers to preventing a disorder, condition, or disease to which such term applies; or to preventing one or more symptoms of such disorder, condition, or disease; or to reversing, alleviating, or inhibiting the progress of such disorder, condition, or disease.

"Treatment" refers to the act of "treating" as defined above.

"Vaccine" refers to a composition that includes an antigen, as defined herein. Administration of the vaccine to a subject results in an immune response, generally against one or more specific diseases. The amount of a vaccine that is therapeutically effective may vary depending on the particular virus used, or the condition of the dog, and can be determined by a veterinary physician. The vaccine may be introduced directly into the subject by the subcutaneous, oral, oronasal, or intranasal routes of administration.

"VANGUARD® Plus 5" is a commercially available vaccine which contains canine distemper (CD) virus, canine adenovirus type 2 (CAV-2), canine parainfluenza (CPI) virus, and canine parvovirus (CPV). "VANGUARD® Plus 5 L4" is a commercially available vaccine which contains CD virus, CAV-2, CPI virus, CPV, and *Leptospira canicola, L. grippotyphosa, L. icterohaemorrhagiae,* and *L. pomona*. "VANGUARD® Plus 5 L4 CV" is a commercially available vaccine which contains CD virus, CAV-2, CPI virus, CPV, canine coronavirus (CCV), and *Leptospira canicola, L. grippotyphosa, L. icterohaemorrhagiae,* and *L. pomona*. The name VANGUARD® is registered and owned by Pfizer, Inc.

DESCRIPTION OF THE INVENTION

Provided herein is a vaccination regimen that reduces morbidity and mortality in animals, and provides increased ease of administration of vaccines for pets, veterinarians, and animal owners. It is highly desirable to administer vaccines using methods that do not require injection when animals are older. Also, oral vaccines are probably less likely to induce undesirable side effects that may be seen after parenteral vaccinations. Oral vaccines can be administered by individuals untrained in administering materials parenterally (i.e., via a needle and syringe), thereby increasing the probable frequency of vaccination and protection from disease.

The invention provides methods of vaccinating a dog with vaccine or immunogenic composition as an aid in preventing or treating disease caused by virulent viral or bacterial strains, including but not limited to 1) canine distemper (CD) caused by canine distemper (CD) virus; 2) infectious canine hepatitis (ICH) caused by canine adenovirus type 1 (CAV-1); 3) respiratory disease caused by canine adenovirus type 2 (CAV-2); 4) canine parainfluenza caused by canine parainfluenza (CPI) virus, and 5) canine parvoviral enteritis caused by canine parvovirus (CPV). Other canine diseases as noted below may also be treated by this invention.

The methods comprise administering to the dog therapeutically effective amounts of a first dose, a second dose, and optionally, a third dose of a composition that is capable of inducing an immune response in the subject. Administration is also given about a year after the first dose as an annual booster. The first dose may be administered subcutaneously or orally. The second dose is administered orally about N days following administration of the first vaccine. Here, N is an integer from about 7 to about 35, inclusive, but is typically an integer from about 14 to about 28, inclusive. The interval between the first and second doses can also be from about 2 to about 4 weeks, with the preferred interval being about 3 weeks.

The methods also include an optional third dose administered orally M days following administration of the second dose. Here, M is an integer of about 7 to about 35, inclusive, but is typically an integer from about 14 to about 28, inclusive. The interval between the second and third doses can also be from about 2 to about 4 weeks, with the preferred interval being about 3 weeks. Thus, from Day 0 (day of administration of the first dose) M would be an integer from about 28 to about 56, inclusive, but is typically an integer from about 35 to about 49, inclusive. The interval between the first and third doses can also be from about 5 to about 7 weeks, with the preferred interval being about 6 weeks.

The methods also include an annual oral administration of a vaccine given about one year following administration of the first vaccine. Generally, this dose is given from about four weeks before to about four weeks after the one-year anniversary of the first vaccine. The attending veterinarian would determine the need for and frequency of any subsequent booster vaccines based on the animal's lifestyle and risk of exposure.

The methods may employ any vaccine that is capable of inducing an immune response in a dog. The route of administration for the vaccines includes subcutaneous, oral, oronasal, and intranasal. The first vaccine is adapted to be administered orally or subcutaneously. The second, third, and annual doses are adapted to be administered orally. Any suitable device may be used to administer the vaccines, including syringes, droppers, needleless injection devices, and the like. For oral administration, a syringe fitted with a cannula may be used to place a dose of the vaccine in the dog's mouth.

In addition to the above administration schedule, the methods also encompass an administration schedule wherein a first dose is administered subcutaneously. A second dose is administered subcutaneously about N days following administration of the first vaccine. Here, N is an integer from about 7 to about 35, inclusive, but is typically an integer from about 14 to about 28, inclusive. The interval between the first and second doses can also be from about 2 to about 4 weeks, with the preferred interval being about 3 weeks. A third dose is administered orally M days following administration of the second dose. Here, M is an integer of about 7 to about 35, inclusive, but is typically an integer from about 14 to about 28, inclusive. The interval between the second and third doses can also be from about 2 to about 4 weeks, with the preferred interval being about 3 weeks. An annual oral administration of a vaccine is given about one year following administration of the first vaccine. Generally, this dose is given from about four weeks before to about four weeks after the one-year anniversary of the first vaccine. The attending veterinarian would determine the need for and frequency of any subsequent booster vaccines based on the animal's lifestyle and risk of exposure. For this administration schedule, the first and second doses are adapted to be administered subcutaneously. The third and annual doses are adapted to be administered orally.

The first, second, third, and annual doses may be the same or a different vaccines or immunogenic composition and each comprises, independently, one or more antigens. The vaccines are based upon live or killed viruses and killed bacterial strains. Useful vaccines thus include live virus vaccines, modified-live virus vaccines, and inactivated virus vaccines, either alone or in combination thereof. Live and modified-live vaccines contain strains that do not cause disease in dogs and have been isolated in non-virulent form or have been attenuated using methods well known in the art, including serial passage in a suitable cell line or exposure to ultraviolet light or a chemical mutagen. Inactivated or killed vaccines contain strains which have been inactivated by known methods, including treatment with formalin, betapropriolactone (BPL), binary ethyleneimine (BEI), or other methods known to those skilled in the art.

The vaccines can contain antigens for immunizing dogs to protect against or treat diseases, including but not limited to 1) canine distemper caused by canine distemper virus; 2) infectious canine hepatitis caused by canine adenovirus type 1; 3) respiratory disease caused by canine adenovirus type 2 or canine respiratory coronavirus; 4) canine parainfluenza caused by canine parainfluenza virus; 5) enteritis caused by canine coronavirus or canine parvovirus; 6) leptospirosis caused by *Leptospira canicola, L. grippotyphosa, L. icterohaemorrhagiae, L. pomona*, or *L. Bratislava*; and 7) infectious tracheobronchitis ("kennel cough") caused by *Bordetella bronchiseptica*. Examples of suitable vaccines include those in the VANGUARD® product line, including but not limited to VANGUARD® Plus 5, VANGUARD® Plus 5 L4, and VANGUARD® Plus 5 L4 CV. One vaccine may be combined with other vaccines to produce a polyvalent vaccine product that can protect dogs against a wide variety of diseases caused by other pathogens. Currently, commercial manufacturers of canine vaccines, as well as end users, prefer polyvalent vaccine products.

For vaccines containing modified live viruses or attenuated viruses, a therapeutically effective dose generally ranges from about $10^2$ $TCID_{50}$ to about $10^{10}$ $TCID_{50}$, inclusive. For specific viruses, a therapeutically effective dose is generally in the following ranges: for CD virus, from about $10^2$ $TCID_{50}$ to about $10^8$ $TCID_{50}$, inclusive; or from about $10^3$ $TCID_{50}$ to about $10^6$ $TCID_{50}$, inclusive; or from about $10^4$ $TCID_{50}$ to about $10^5$ $TCID_{50}$, inclusive; for CAV-2, from about $10^2$ $TCID_{50}$ to about $10^8$ $TCID_{50}$, inclusive; or from about $10^3$ $TCID_{50}$ to about $10^6$ $TCID_{50}$, inclusive; or from about $10^4$ $TCID_{50}$ to about $10^5$ $TCID_{50}$, inclusive; for CPV, from about $10^3$ $TCID_{50}$ to about $10^{10}$ $TCID_{50}$, inclusive; or from about $10^6$ $TCID_{50}$ to about $10^9$ $TCID_{50}$, inclusive; or from about $10^7$ $TCID_{50}$ to about $10^8$ $TCID_{50}$, inclusive; and for CPI virus, from about $10^3$ $TCID_{50}$ to about $10^{10}$ $TCID_{50}$, inclusive; or from about $10^5$ $TCID_{50}$ to about $10^9$ $TCID_{50}$, inclusive; or from $10^6$ $TCID_{50}$ to about $10^8$ $TCID_{50}$, inclusive. The amount of CCV in an inactivated viral preparation should be at least about 100 relative units per dose, and preferably in the range from about 1,000 to about 4,500 relative units per dose.

For vaccines containing a bacterin, a therapeutically effective dose for each Leptospiral species in the vaccine generally is in the range from about 100 nephelometric units (NU) to about 3,500 NU per vaccine dose, and preferably in the range from about 200 NU to about 2,000 NU per dose. A therapeutically effective dose for *Bordetella bronchiseptica* in the vaccine generally is in the range from about $3 \times 10^6$ to about $3 \times 10^{11}$ cells inclusive; or from about $3 \times 10^7$ to about $3 \times 10^{10}$ cells inclusive; or from about $3 \times 10^8$ to about $3 \times 10^9$ cells inclusive.

Other components of vaccines may include pharmaceutically acceptable excipients, including carriers, solvents, and diluents, isotonic agents, buffering agents, stabilizers, preservatives, immunomodulatory agents (e.g., interleukins, interferons, and other cytokines), vaso-constrictive agents, antibacterial agents, antifungal agents, and the like. Typical carriers, solvents, and diluents include water, saline, dextrose, ethanol, glycerol, and the like. Representative isotonic agents include sodium chloride, dextrose, mannitol, sorbitol, lactose, and the like. Useful stabilizers include gelatin, albumin, and the like.

As used herein, "a pharmaceutically acceptable carrier" includes any and all solvents, dispersion media, coatings, adjuvants, stabilizing agents, diluents, preservatives, antibacterial and antifungal agents, isotonic agents, adsorption delaying agents, and the like. The carrier(s) must be "acceptable" in the sense of being compatible with the components of the invention and not deleterious to the subject to be immunized. Typically, the carriers will be will be sterile and pyrogen-free, and selected based on the mode of administration to be used. It is well known by those skilled in the art that the preferred formulations for the pharmaceutically accepted carrier which comprise the vaccines are those pharmaceutical carriers approved in the applicable regulations promulgated by the United States (US) Department of Agriculture, or equivalent government agency in a non-US country. Therefore, the pharmaceutically accepted carrier for commercial production of the vaccines is a carrier that is already approved or will be approved by the appropriate government agency in the US or foreign country.

The vaccine compositions optionally may include vaccine-compatible pharmaceutically acceptable (i.e., sterile and non-toxic) liquid, semisolid, or solid diluents that serve as pharmaceutical vehicles, excipients, or media. Diluents can include water, saline, dextrose, ethanol, glycerol, and the like. Isotonic agents can include sodium chloride, dextrose, mannitol, sorbitol, and lactose, among others. Stabilizers include albumin, among others.

The vaccines can further be mixed with one or more adjuvants that are pharmaceutically acceptable. Many such adjuvants are known in the art. Representative adjuvants include oil-based adjuvants, such as Freund's Complete Adjuvant and Freund's Incomplete Adjuvant, mycolate-based adjuvants (e.g., trehalose dimycolate), bacterial lipopolysaccharides, peptidoglycans (i.e., mureins, mucopeptides, or glycoproteins such as N-Opaca, muramyl dipeptide or analogs thereof), proteoglycans (e.g., extracted from *Klebsiella pneumoniae*), streptococcal preparations (e.g., OK432), BIOSTIM® (e.g., 01K2), Iscoms (e.g., see European Patent Application Nos. EP 109942, EP 180564 and EP 231039), aluminum hydroxide, saponin, diethylaminoethyl (DEAE)-dextran, neutral oils (e.g., miglyol), vegetable oils (e.g., *arachis* oil), liposomes, PLURONIC® polyols. Other adjuvants include the R1131 adjuvant system, alum, aluminum hydroxide gel, cholesterol, oil-in-water emulsions, water-in-oil emulsions, block co-polymer (CytRx, Atlanta Ga.), SAF-M (Chiron, Emeryville Calif.), lecithin in oil (e.g., AMPHIGEN® adjuvant), saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *Escherichia coli* (recombinant or otherwise), cholera toxin, or muramyl dipeptide, among others.

The immunogenic compositions can further include one or more other immunomodulatory agents such as, e.g., interleukins, interferons, or other cytokines. The immunogenic compositions can also antibiotics, including gentamicin and Merthiolate.

Dose sizes of the vaccines typically range from about one-tenth mL to about five mL, inclusive. Typically, a dose of about one mL is used for the oral vaccines. Each dose contains a therapeutically effective amount of the antigen or antigens that may vary depending on the age and general condition of the dog, the route of administration, the nature of the antigen, and other factors. The amounts and concentrations of the other components of the vaccines may be adjusted to modify the physical and chemical properties of the vaccines, and can readily be determined by the skilled artisan. For example, adjuvants typically comprises from about 25 µg to about 1000 µg, inclusive, of a one-mL dose. Similarly, antibiotics typically comprise from about one µg to about 60 µg, inclusive, of a one-mL dose.

One skilled in the art can readily formulate a vaccine. The vaccines are provided sterile and pyrogen-free. The immunogenic compositions can be made in various forms depending upon the route of administration, storage requirements, and the like. For example, the immunogenic compositions can be made in the form of sterile aqueous solutions or dispersions suitable for injectable use, or made in lyophilized forms using freeze-drying techniques. Lyophilized immunogenic compositions can be reconstituted prior to use in a stabilizing solution, e.g., saline or/and HEPES, with or without adjuvant.

The subjects suitable for vaccination would include dogs that are about four weeks of age or older. Thus, the first dose would be given to a dog at about four weeks of age, followed by subsequent doses according to the timetable given herein. Certain commercially prepared vaccines provide directions for the timing of administration and number of doses based on the potential for maternal antibody interference. For example, the product label for VANGUARD® Plus 5 L4 (Pfizer Inc) indicates that dogs receiving the first vaccine at less than 9 weeks of age should be administered a third orally administered one-ml dose at about three weeks after a second dose.

EXAMPLES

The following examples are intended to be illustrative and non-limiting, and represent a few specific embodiments of the present invention.

Example 1

This study evaluated the ability of a modified live vaccine to cause seroconversion (e.g., going from a state of having no antibodies to a state of having relatively high concentrations of antibodies to specific antigens) when a vaccine was administered subcutaneously in a first dose, then orally in a second and third dose.

Antigens of interest are Canine Adenovirus-Type 1 (CAV-1), Canine Parvovirus (CPV), and Canine Distemper Virus (CDV). Thirty-three pups between the ages of 6 and 9 weeks at the initiation of the study that had no antibodies to CAV-1, CPV or CDV were randomly divided into three treatment groups of 11 dogs each. Dogs in treatment group T01 were given placebo vaccine three times, three weeks apart. This treatment group was included to ensure that animals were not exposed to viruses of interest in any way except through experimental vaccination. Animals in treatment groups T02 and T03 were given experimental vaccines first subcutaneously (on day 0), then the same vaccine orally three weeks (day 21) and six weeks (day 42) later. The only difference between T02 and T03 was the amount of virus in the vaccines administered, with T02 receiving a relatively low dose, and T03 receiving a relatively high dose. Blood samples were taken weekly to measure concentrations (e.g., titers) of specific antibodies. Serum samples were analyzed for serum antibodies against CDV, CPV, and CAV1 according to standard procedures. Presented in Tables 1 and 2 are details of the experimental design and the Investigational Veterinary Product (IVP).

TABLE 1

Experimental Design

| Group | N | Vaccination | | | Serum Collection |
|---|---|---|---|---|---|
| | | Day 0 | Day 21 | Day 42 | |
| T01 Negative Control | 11 | SQ saline | Oral saline | Oral saline | Days 0, 7, 14, 21, 28, 35, 42, 49, 56, and 63 |
| T02 | 11 | SQ "low" titer | Oral "low" titer | Oral "low" titer | |
| T03 | 11 | SQ "high" titer | Oral "high" titer | Oral "high" titer | |

SQ = subcutaneous

TABLE 2

Investigational Veterinary Product (IVP)

| IVP | Vaccine Serial | Approximate Input Viral Titers per Dose (log) | Number of Doses | Volume per Dose |
|---|---|---|---|---|
| CDV-CAV$_2$-CPV-CPI at low titer | L031006C (diluted 100X) | CDV: 2.7 CAV$_2$: 2.2 CPV: 6.0 CPI: 5.9 | T01 = 0 T02 = 33 T03 = 0 Total = 33 | Approx. 1 mL |

TABLE 2-continued

| | | Investigational Veterinary Product (IVP) | | |
|---|---|---|---|---|
| IVP | Vaccine Serial | Approximate Input Viral Titers per Dose (log) | Number of Doses | Volume per Dose |
| CDV-CAV$_2$-CPV-CPI at relatively high titer | L031006C | CDV: 4.7<br>CAV$_2$: 4.2<br>CPV: 8.0<br>CPI: 7.9 | T01 = 0<br>T02 = 0<br>T03 = 33<br>Total = 33 | Approx. 1 mL |

All animals in T01 remained essentially free of antibodies to the antigens of interest, indicating that there was no environmental exposure to these viruses. Animals in T02 and T03 responded similarly to the vaccines, indicating that the dose did not significantly influence patterns of responses. Regardless of antigen, animals given experimental vaccine (groups T02 and T03) responded robustly to the first (subcutaneously administered) vaccine dose. For comparison and perspective, animals are considered protected from disease when they have antibody titers greater than or equal to 1:16 for CAV-1, 1:32 for CDV and 1:80 for CPV.

Figure 1:
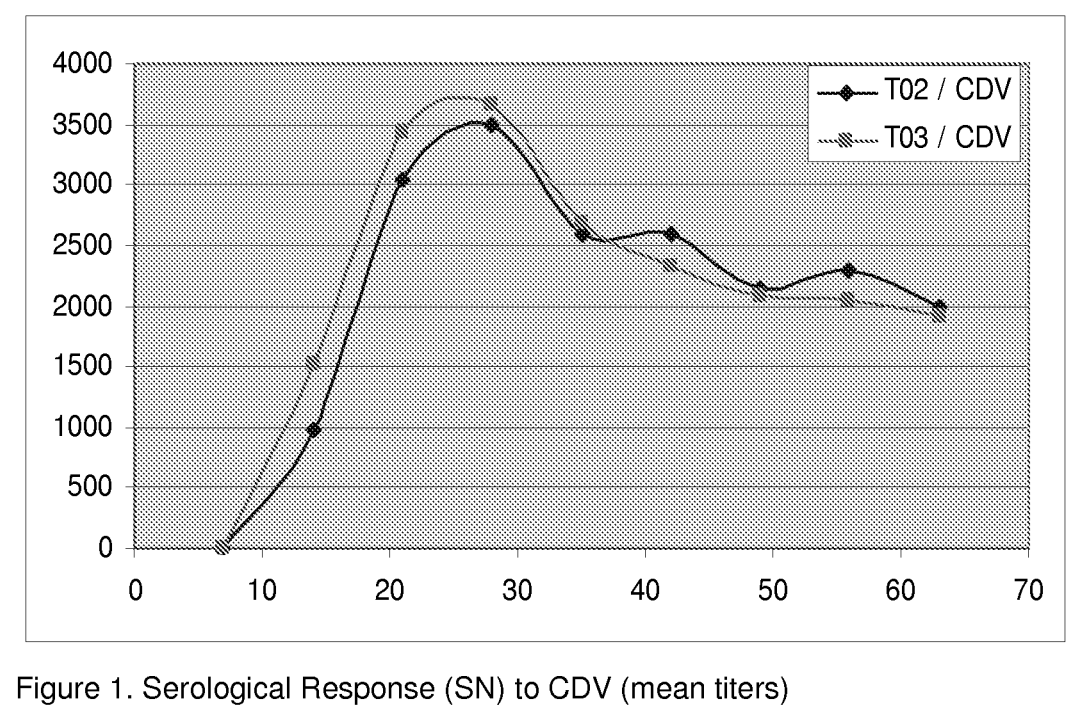

CDV-specific antibodies peaked at 28 days after the first vaccination, with mean titers of 1:3499 and 1:3668 for T02 and T03 respectively (see FIG. 1). In the case of CDV-specific titers following subcutaneous vaccination, this concentration of antibodies may have been high enough to interfere with the animals' abilities to subsequently react to orally administered vaccines. Specific antibodies against CPV followed a similar pattern, although the peak antibody titers occurred two weeks following the 1$^{st}$ oral vaccination (mean titer of 1:5702 on day 36) for dogs in T02, and one week following the 1$^{st}$ oral vaccination (mean titer of 1:5613 on day 28) for dogs in T03 (see FIG. 2).

Due to the differences in timing between CDV and CPV peak antibody concentrations, this pattern could be interpreted as an immune response to the oral vaccination, although the initial high antibody titers again make interpretation difficult. However, specific antibodies against CAV-1 clearly indicate that there is a robust immune response to oral dosing for this antigen (see FIG. 3). On the day of the first oral vaccination, day 21, animals in T02 had mean titers of CAV-1 specific antibodies of 1:5, and those in T03 had mean titers of 1:16. Two weeks later, dogs had mean antibody titers of 1:25 and 1:118 in groups T02 and T03, respectively. Even more remarkable, two weeks following the 2$^{nd}$ orally administered vaccine, on day 56, animals had mean titers of 1:83 and 1:150 in T02 and T03 respectively. Traditionally CAV-1 antibody titers are lower than the other two antigens, which may have decreased the likelihood of interference caused by subcutaneous vaccination.

While high titers of antibodies specific for CDV and CPV following a subcutaneous vaccination make clear interpretation of the efficacy of oral dosing for CDV and CPV difficult, the conclusion from this study is that dogs are capable of seroconversion in response to subcutaneous vaccination followed by oral vaccination. A secondary conclusion is that oral vaccination is a practical and potentially effective route of vaccine administration for dogs.

Example 2

This study evaluated the ability of a modified live vaccine to cause seroconversion (e.g., going from a state of having no antibodies to a state of having relatively high concentrations of antibodies to specific antigens) when a vaccine was administered subcutaneously or orally in a first dose, then orally in a second and third dose.

Thirty-nine pups, between the ages of 6 and 10 weeks at the initiation of the study, and having no antibodies to Canine Adenovirus-Type 1 (CAV-1), Canine Parvovirus (CPV), Canine Distemper Virus (CDV), or Canine Parainfluenza (CPI), were randomly divided into three treatment groups of 13 dogs each. Dogs in treatment group T01 were orally given placebo vaccine three times, three weeks apart. This treatment group was included to ensure that animals were not exposed to viruses of interest in any way but through experimental vaccination. Animals in treatment group T02 were orally given the same experimental vaccine on days 0, 21, and 42. Animals in treatment group T03 were subcutaneously given experimental vaccine on day 0, then the same vaccine orally three weeks (day 21) and six weeks (day 42) later. The only difference between T02 and T03 was that T02 received the first dose orally, and T03 received the first dose subcutaneously. Blood samples were taken weekly to measure concentrations (e.g., titers) of specific antibodies. Serum samples were analyzed for serum antibodies against CDV, CPV and CAV-1 according to standard procedures. (Animals vaccinated with CAV-2 generate antibodies cross-reactive with CAV-1.) Animals were considered positive responders (i.e., protected from disease) if they had antibody titers greater than or equal to 1:16 for CAV-1, 1:32 for CDV, and 1:16 for CPV. Presented in Tables 3 and 4 are details of the experimental design and the Investigational Veterinary Product (IVP).

TABLE 3

| | | Experimental Design | | | |
|---|---|---|---|---|---|
| | | Vaccination | | | Serum |
| Group | N | Day 0 | Day 21 | Day 42 | Collection |
| T01<br>Negative<br>Control | 13 | Oral<br>Vehicle | Oral<br>Vehicle | Oral<br>Vehicle | Days 0, 7,<br>14, 21, 28,<br>35, 42, 49,<br>56, and 63 |
| T02 | 13 | Oral IVP | Oral IVP | Oral IVP | |
| T03 | 13 | SQ IVP | Oral IVP | Oral IVP | |

SQ = subcutaneous
IVP = Investigational Veterinary Product

TABLE 4

| | | Investigational Veterinary Product (IVP) | | |
|---|---|---|---|---|
| IVP | Vaccine Serial | Approximate Input Viral Titers per Dose (log) | Number of Doses | Volume per Dose |
| CDV-CAV$_2$-CPV-CPI at high titer | L25Aug06C plus CDV prep #71802 | CDV: 3.5<br>CAV$_2$: 4.0<br>CPV: 7.1<br>CPI: 5.2 | T01 = 0<br>T02 = 39<br>T03 = 39<br>Total = 78 | Approx. 1 mL |

As presented in Table 5, all animals in the T03 group (SQ, oral, oral) seroconverted against the three measured viruses by Day 63. All animals in the T02 group (oral, oral, oral) seroconverted against CPV and CAV-1 by Day 63. Approximately half of the animals in the T02 group seroconverted to CDV by Day 63, suggesting that changes to the current formulation may be possible. Thus, these results demonstrate that oral dosing is an effective approach to vaccination.

TABLE 5

Seroconversion Results

| Seroconversion | | Day of Study | | |
|---|---|---|---|---|
| Results | | 21 | 42 | 63 |
| CPV | T01 | 0/13 | 0/13 | 0/13 |
| | T02 | 7/13 | 10/13 | 13/13 |
| | T03 | 13/13 | 13/13 | 13/13 |
| CDV | T01 | 0/13 | 0/13 | 0/13 |
| | T02 | 5/13 | 6/13 | 6/13 |
| | T03 | 13/13 | 13/13 | 13/13 |
| CAV1 | T01 | 5/13 | 11/13 | 10/13 |
| | T02 | 12/13 | 13/13 | 13/13 |
| | T03 | 6/13 | 13/13 | 13/13 |

Example 3

This notional example describes the administration to dogs of a Canine Distemper-Adenovirus Type 2-Parainfluenza-Parvovirus Modified Live Virus Vaccine. A freeze-dried preparation of the vaccine is aseptically rehydrated with sterile diluent and shaken well, according to the label instructions. An example of such a vaccine is VANGUARD® Plus 5 (Pfizer Inc). This vaccine contains attenuated strains of CD virus (approximately $10^5$ $TCID_{50}$), CAV-2 (approximately $10^4$ $TCID_{50}$), CPI virus (approximately $10^8$ $TCID_{50}$), and CPV (approximately $10^8$ $TCID_{50}$) propagated on an established canine cell line.

Healthy dogs at 4 weeks of age or older are administered a 1-ml first dose of the reconstituted vaccine either orally or subcutaneously. The dogs are orally given a 1-ml second dose about three weeks after the first vaccine, followed by a third orally administered 1-ml dose at about three weeks after the second dose. The dogs are given an annual orally administered 1-ml booster vaccine at about one year after the first vaccine. The attending veterinarian determines the need for and frequency of any subsequent booster vaccine based on the animal's lifestyle and risk of exposure.

Example 4

This notional example describes the administration to dogs of a Canine Distemper-Adenovirus Type 2-Parainfluenza-Parvovirus Modified Live Virus Vaccine containing a Leptospira Canicola-Grippotyphosa-Icterohaemorrhagiae-Pomona Bacterin. A freeze-dried preparation of the vaccine is aseptically rehydrated with sterile diluent and shaken well, according to the Label instructions. An example of such a vaccine is VANGUARD® Plus 5 L4 (Pfizer Inc). This vaccine is a freeze-dried preparation of attenuated strains of CD virus (approximately $10^5$ $TCID_{50}$), CAV-2 (approximately $10^4$ $TCID_{50}$), CPI virus (approximately $10^8$ $TCID_{50}$), CPV (approximately $10^8$ $TCID_{50}$), and inactivated whole cultures of L. canicola, L. grippotyphosa, L. icterohaemorrhagiae, and L. pomona. An adjuvanted sterile gel is used to rehydrate the freeze-dried component, which is packaged with inert gas in place of vacuum.

Healthy dogs at 4 weeks of age or older are administered a 1-ml first dose of the reconstituted vaccine either orally or subcutaneously. The dogs are orally given a 1-ml second dose about three weeks after the first. Dogs receiving the first vaccine at less than 9 weeks of age are administered a third orally administered 1-ml dose at about three weeks after the second dose. The dogs are given an annual orally administered 1-ml booster vaccine at about one year after the first vaccine. The attending veterinarian determines the need for and frequency of any subsequent booster vaccines based on the animal's lifestyle and risk of exposure.

Example 5

This notional example describes the administration to dogs of a Canine Distemper-Adenovirus Type 2-Coronavirus-Parainfluenza-Parvovirus Vaccine containing a Leptospira Canicola-Grippotyphosa-Icterohaemorrhagiae-Pomona Bacterin.

A freeze-dried Canine Distemper-Adenovirus Type 2-Parainfluenza-Parvovirus Modified Live Virus Vaccine containing a Leptospira Canicola-Grippotyphosa-Icterohaemorrhagiae-Pomona Bacterin (for example VANGUARD® Plus 5 L4, see Example 4) is aseptically rehydrated with a liquid coronavirus vaccine and shaken well, according to the Label instructions. An example of such a coronavirus vaccine is a liquid preparation of inactivated canine coronavirus (CCV) with an adjuvant. The combination of VANGUARD® Plus 5 L4 and a CCV vaccine is sold by Pfizer as VANGUARD® Plus 5 L4 CV.

Healthy dogs at 4 weeks of age or older are administered a 1-ml first vaccine of the reconstituted vaccine either orally or subcutaneously. The dogs are orally given a 1-ml second dose of the combined vaccine about three weeks after the first vaccine. The dogs are orally given a 1-ml dose of only the coronavirus vaccine about three weeks after the second dose. Dogs receiving the first vaccine at less than 9 weeks of age receive a second orally administered 1-ml dose of the combined vaccine (in place of the coronavirus vaccine) at about three weeks after the second vaccine. The dogs are given an annual orally administered 1-ml booster of the combined vaccine at about one year after the priming vaccine. The attending veterinarian determines the need for and frequency of any subsequent booster vaccines based on the animal's lifestyle and risk of exposure.

Example 6

This notional example describes the administration to dogs of a Canine Distemper-Adenovirus Type 2-Parainfluenza-Parvovirus Modified Live Virus Vaccine containing a Bordetella bronchiseptica Bacterin. A freeze-dried preparation of the vaccine is aseptically rehydrated with a liquid diluent containing inactivated whole cultures of B. bronchiseptica and shaken well, according to the Label instructions. An example of such a vaccine is VANGUARD® Plus 5 (see Example 4). An example of such a diluent is a liquid preparation of an inactivated culture of B. bronchiseptica.

Healthy dogs at 4 weeks of age or older are administered a 1-ml first vaccine of the reconstituted vaccine either orally or subcutaneously. The dogs are orally given a 1-ml second dose of the vaccine from about two to about four weeks after the first vaccine. Dogs receiving the first vaccine at less than four months of age receive a third orally administered 1-ml dose of the vaccine at about four months of age. The dogs are given an annual orally administered 1-ml booster of the vaccine at about one year after the priming vaccine. Subsequent oral 1-ml booster vaccines are administered annually. Where B. bronchiseptica and canine virus exposure is likely, such as breeding, boarding, and showing situations, an additional booster may be indicated or annual revaccination should be timed 2 to 4 weeks prior to these events.

It should be noted that, as used in this specification and the appended claims, singular articles such as "a," "an," and "the," may refer to one object or to a plurality of objects unless the context clearly indicates otherwise. Thus, for example, reference to a composition containing "a compound" may include a single compound or two or more compounds.

It is to be understood that the above examples and descriptions are intended to be illustrative and not restrictive. Many embodiments will be apparent to those of skill in the art upon reading the above description. The scope of the invention should, therefore, be determined with reference to the appended claims, along with the full scope of equivalents to which such claims are entitled.

All of the methods disclosed and claimed herein can be executed without undue experimentation in light of the present disclosure. While the methods of this invention have been described in terms of various embodiments, it will be apparent to those of skill in the art that variations may be applied to methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of eliciting protective titer against Canine Distemper (CD) virus in a serum of a dog comprising administering to the dog therapeutically effective amounts of vaccine, wherein the vaccine comprises modified live or attenuated Canine Distemper (CD) Virus, wherein the vaccine is administered orally in a first dose, orally in a second dose, and orally in one or more annual doses, wherein said protecting titer against CD is greater than or equal to 1:32 at three weeks after said second vaccination.

2. The method of claim 1 wherein said vaccine further comprises one or more of Canine Adenovirus-2 (Cav-2), and Canine Parvovirus (CPV).

3. The method of claim 2, wherein said Adenovirus-2 (Cav-2), and Canine Parvovirus (CPV) are attenuated or modified live viruses.

4. The method of claim 3, wherein said vaccine further comprises Canine Parainfluenza Virus (CPI).

5. The method of claim 3, wherein said vaccine is not adjuvanted.

6. The method according to claim 3, wherein the vaccine further comprises a bacterin selected from the group consisting of *Bordetella bronchiseptica, Leptospira canicola, L. grippotyphosa, L. icterohaemorrhagiae*, and *L. pomona*.

7. The method according to claim 1, wherein the vaccine further comprises a bacterin selected from the group consisting of *Bordetella bronchiseptica, Leptospira canicola, L. grippotyphosa, L. icterohaemorrhagiae*, and *L. pomona*.

8. The method of claim 1, wherein said vaccine is not adjuvanted.

9. The method according to claim 1, wherein the viral antigens are CD virus, CAV-2, CPI virus, and CPV, and the bacterium in the bacterin is *Bordetalla bronchiseptica*.

10. The method according to claim 1, wherein said vaccine is not adjuvanted.

11. The method according to claim 1, wherein the CD antigen is in the range of between present in the following ranges of amounts: for CD virus, about $10^2TCID_{50}$ to about $10^8TCID_{50}$, inclusive.

12. A method according to claim 1, wherein the second dose is administered from 7 to 35 days, inclusive, after the first dose.

13. A method according to claim 1, further comprising orally administering a third dose of said vaccine, wherein the third dose is administered from 7 to 35 days, inclusive, after the second dose.

14. A method according to claim 1, wherein a first annual dose is administered about one year after the first dose.

* * * * *